(12) United States Patent
Inada et al.

(10) Patent No.: US 6,171,266 B1
(45) Date of Patent: Jan. 9, 2001

(54) MASSAGING APPARATUS HAVING DIAGNOSTIC CAPABILITY

(75) Inventors: Nichimu Inada; Koji Goto, both of Osaka (JP)

(73) Assignee: Family Kabushiki Kaisha, Osaka (JP)

( * ) Notice: Under 35 U.S.C. 154(b), the term of this patent shall be extended for 0 days.

(21) Appl. No.: 09/173,711

(22) Filed: Oct. 16, 1998

(30) Foreign Application Priority Data

Aug. 27, 1998 (JP) .................................................. 10-242262

(51) Int. Cl.[7] .................................................. A61H 15/00
(52) U.S. Cl. ........................... 601/99; 601/100; 601/101; 601/102; 601/103; 601/111; 601/116
(58) Field of Search .................................. 601/46, 49–56, 601/70, 86, 87, 90, 93.5, 98–103, 115, 116

(56) References Cited

U.S. PATENT DOCUMENTS

| | | | |
|---|---|---|---|
| 5,207,621 | * | 5/1993 | Koch et al. . |
| 5,741,218 | * | 4/1998 | Fujii .................................... 601/100 |
| 5,857,986 | * | 1/1999 | Moriyasu . |
| 5,993,401 | * | 11/1999 | Inbe et al. . |

FOREIGN PATENT DOCUMENTS

| | | | |
|---|---|---|---|
| 04138160 | * | 5/1992 | (JP) . |
| 9723254 | * | 7/1997 | (WO) . |

* cited by examiner

Primary Examiner—Danton D. DeMille
(74) Attorney, Agent, or Firm—Oblon, Spivak, McClelland, Maier & Neustadt, P.C.

(57) ABSTRACT

An improved massaging apparatus includes a massaging element for performing a massaging action, a drive mechanism for driving the massaging element, diagnostic inquiry means for addressing a diagnostic inquiry to a user, input means for inputting a user's answer to the diagnostic inquiry, judgment means for judging the physical condition of the user based on the user's answer, setting means for setting massaging conditions of a massage operation based on the judgment made by the judgment means, and execution means for causing the drive mechanism to drive the massaging element according to the massaging conditions set by the setting means.

20 Claims, 10 Drawing Sheets

| | | | | | |
|---|---|---|---|---|---|
| NONAUTOMATIC COURSE IN OPERATION | | | | | |
| UPPER HALF BODY | VERTICAL MOTION | ROLLING | | POINTING | |
| | | PULLING | | VERTICAL | |
| | KNEADING | | | | |
| | FINGER PRESSURE | UPPER HEADS | LOWER HEADS | CROSS KNEADING | |
| | RIGHT/LEFT | SIMULTANEOUS | | ALTERNATE | |
| | RHTYHM | NORMAL | | RHYTHMIC | |
| | POWER | LOW | MEDIUM | HIGH | |
| | VIBRATION | NORMAL | WAVE 1 | WAVE 2 | |
| | POWER | LOW ▨▨▨▨▨▨▨▨▨▨▨ ▯ ▯ HIGH | | | |
| LOWER HALF BODY | MODE POINT POWER | AUTOMATIC | | | |
| | | FEET | THIGHS | HIPS | |
| | | LOW | MEDIUM | HIGH | |
| TIMER | | 15 MIN | | 30 MIN | |

DIAGNOSTIC INQUIRY COURSE

CHOOSE YES OR NO.

DO YOU FEEL STIFF IN THE SHOULDERS MORE FREQUENTLY THAN BEFORE ?

[ YES ]  [ NO ]

DIAGNOSTIC INQUIRY COURSE

CHOOSE YES OR NO.

ARE YOU IN ANY ONE OF THE FOLLOWING CONDITIONS ?
* UNDER MEDICAL TREATMENT DIRECTED BY A DOCTOR
* HAVING A HEART TROUBLE
* HAVING A FEVER
* BEING A PREGNANT
* HAVING SOMETHING WRONG IN THE BACKBONE

[ YES ]  [ NO ]

DIAGNOSTIC INQUIRY COURSE

YOUR CURRENT PHYSICAL CONDITION IS JUDGED TO BE ∗∗∗∗∗∗∗∗∗∗∗∗∗∗∗∗∗∗.

A MASSAGING COURSE BEST-SUITED TO YOU NOW HAS BEEN SET.

DO YOU WISH TO EXECUTE IT ?

[ YES ]  [ NO ]

MASSAGING APPARATUS HAVING DIAGNOSTIC CAPABILITY

BACKGROUND OF THE INVENTION

1. Field of the Invention

The present invention relates to a massaging apparatus capable of addressing diagnostic inquiries to a user for performing a proper massage based on the physical condition of the user.

2. Description of the Related Art

Recently, massaging apparatus have been provided with multiple massaging functions such as kneading, pressing, tapping and vibration. Further, there has been proposed a chair-type massaging apparatus which is adapted to massage the whole body (including the lower half of the body) of a user by activating massaging elements provided in the backrest portion, seat portion and footrest portion thereof. Such massaging apparatus are intended not only to provide a mere massage but only to achieve certain therapeutic objectives such as maintenance of health and recovery of functions.

With such conventional massaging apparatus, however, the user selects the type of massage to be performed and determines a portion to be massaged by himself or herself according to his or her own preference or based on a subjective symptom perceived by the user. Thus, where the user's judgment is improper or the user cannot judge based on his or her own knowledge, a proper massage based on the current physical condition of the user is not necessarily performed.

It is, therefore, an object of the present invention to provide a massaging apparatus which is capable of judging the current physical condition of a user and providing a proper massage based on the judgment.

SUMMARY OF THE INVENTION

According to the present invention, there is provided a massaging apparatus comprising a massaging element for performing a massaging action, a drive mechanism for driving the massaging element, diagnostic inquiry means for addressing a diagnostic inquiry to a user, input means for inputting a user's answer to the diagnostic inquiry, judgment means for judging the physical condition of the user based on the user's answer, setting means for setting massaging conditions of a massage operation based on the judgment made by the judgment means, and execution means for causing the drive mechanism to drive the massaging element according to the massaging conditions set by the setting means.

With this construction, the judgment means judges the current physical condition of a user and the setting means sets massaging conditions of a massage operation based on the current physical condition of the user thus judged, whereby a proper massage accommodated to the current physical condition of the user can be provided and, hence, enhanced therapeutic effects can be obtained by the massage.

The wording "setting massaging conditions of a massage operation" herein is meant to include selecting one of predetermined massaging courses, or determining portions to be massaged (neck, shoulders, waist and the like), type of massage (kneading, tapping or the like) to be performed, massaging time and like conditions either individually or in combination. The massage courses termed in the present invention each include a fixed massaging procedure which is automatically performed.

The judgment means is preferably capable of judging the physical condition of the user to be contraindicating any massage. Where the user must not be massaged for the reason that, for example, he or she is under a medical treatment directed by a doctor or has a heart trouble, the judgment means judges the physical condition of the user to be contraindicating any massage and in response thereto the setting means does not set any massaging condition. With this feature, the user is prevented from inadvertently actuating the massaging element.

The massaging apparatus according to the present invention may be provided with output means for outputting information on the physical condition of the user based on the judgment made by the judgment means so as to let the user know the information. Thus, it is possible for the user to know his or her current physical condition judged by the judgment means.

The foregoing and other objects, features and attendant advantages will be readily appreciated as the same becomes better understood by reference to the following detailed description when considered in connection with the accompanying drawings in which:

BRIEF DESCRIPTION OF THE DRAWINGS

FIG. 6 shows images which can be displayed on the display part of the massaging apparatus, in which FIG. 6(c) shows an image presenting information on a nonautomatic massaging course in operation;

FIG. 7 shows images which can be displayed on the display part of the massaging apparatus, in which

FIG. 8 shows images which can be displayed on the display part of the massaging apparatus, in which FIG. 8(a) shows an image presenting an exemplary diagnostic inquiry; FIG. 8(b) shows an image presenting another exemplary diagnostic inquiry (concerning massage contraindicating items); and FIG. 8(c) shows an image presenting a diagnosis; and FIG. 9 shows images which can be displayed on the display part of the massaging apparatus, in which

DETAILED DESCRIPTION OF THE PREFERRED EMBODIMENT

The present invention will now be described in detail with reference to a preferred embodiment thereof.

Figure 1:
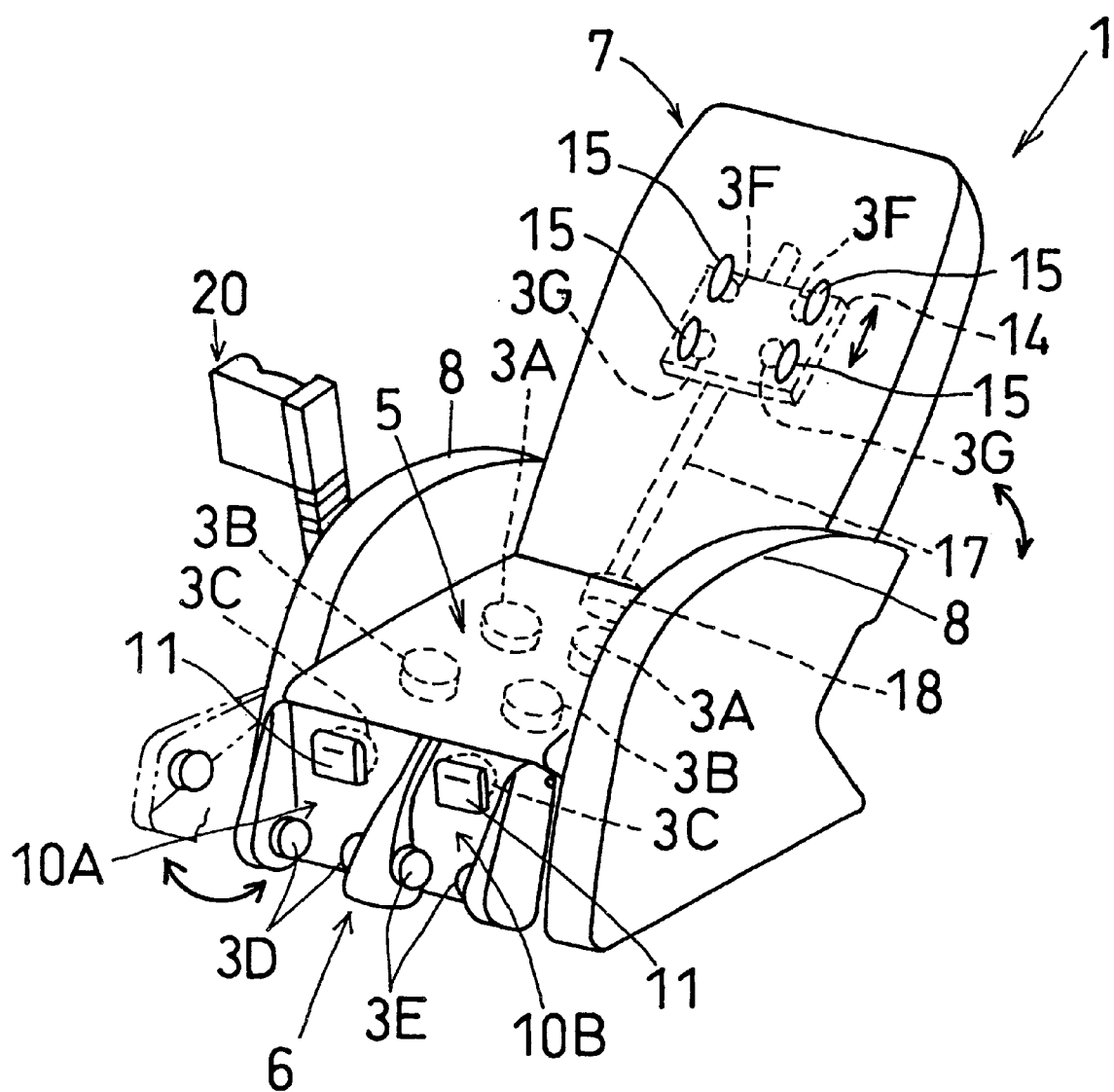
FIG. 1 is a schematic perspective view showing the overall construction of a massaging apparatus according to the present invention.

Referring first to FIG. 1, there is shown massaging apparatus 1 according to the present invention in which air cells 3 are disposed at different portions of a chair-type apparatus body. When actuated, the air cells 3 expand and contract, so that different portions of the user are massaged. The apparatus body includes a seat portion 5, a footrest portion 6 situated forwardly of the seat portion 5, a backrest portion 7 extending upwardly from the rear side of the seat portion 5, and a pair of armrest portions 5 respectively situated on opposite lateral sides of the seat portion 5.

The air cells 3 expand and contract when air is supplied thereto and discharged therefrom by an air source (not shown). The air supply/discharge switching for each air cell is achieved by the use of a change-over valve (not shown). In the seat portion 5 are disposed a pair of air cells 3A adjacent the rear side thereof for pressing the hips of the user and a pair of air cells 3B adjacent the front side thereof for pressing the thighs of the user.

The footrest portion 6 includes a pair of foot receiving portions 10A and 10B shaped like troughs for receiving respective feet of the user. Air cell 3C is located in the bottom of each foot receiving portion on the side adjacent the seat portion 5. Further, a pair of air cells 3D and a pair of air cells 3E are located on the foot receiving portions 10A and 10B, respectively, at their confronting walls adjacent the forward ends thereof. The air cells 3C, 3D and 3E of the footrest portion 6 are adapted to massage the feet of the user by their expansion and contraction. Specifically, the air cells 3C are adapted to press the calves of the user from below through respective massaging heads 11, while the air cells 3D and 3C are adapted to press the ankles of the user in a sandwiching manner.

In the backrest portion 7 is located a movable support 14 which is upwardly and downwardly slidable therewithin. The movable support 14 is provided with a pair of upper air cells 3F and a pair of lower air cells 3G, which pairs are adapted to massage the neck and the back of the user by operating respective massaging heads 15 by their expansion and contraction. The upward and downward sliding of the movable support 14 is achieved by a feed screw mechanism comprising a longitudinally extending screw shaft 17 and a nut member (not shown) secured to the rear side of the movable support 14 and threadingly engaging the screw shaft 17. The screw shaft 17 is rotated by an up/down drive unit (motor) 18 to cause the movable support 14 to slide upwardly and downwardly.

The backrest portion 7 is reclinable by an electric motor (not shown).

Figure 2:
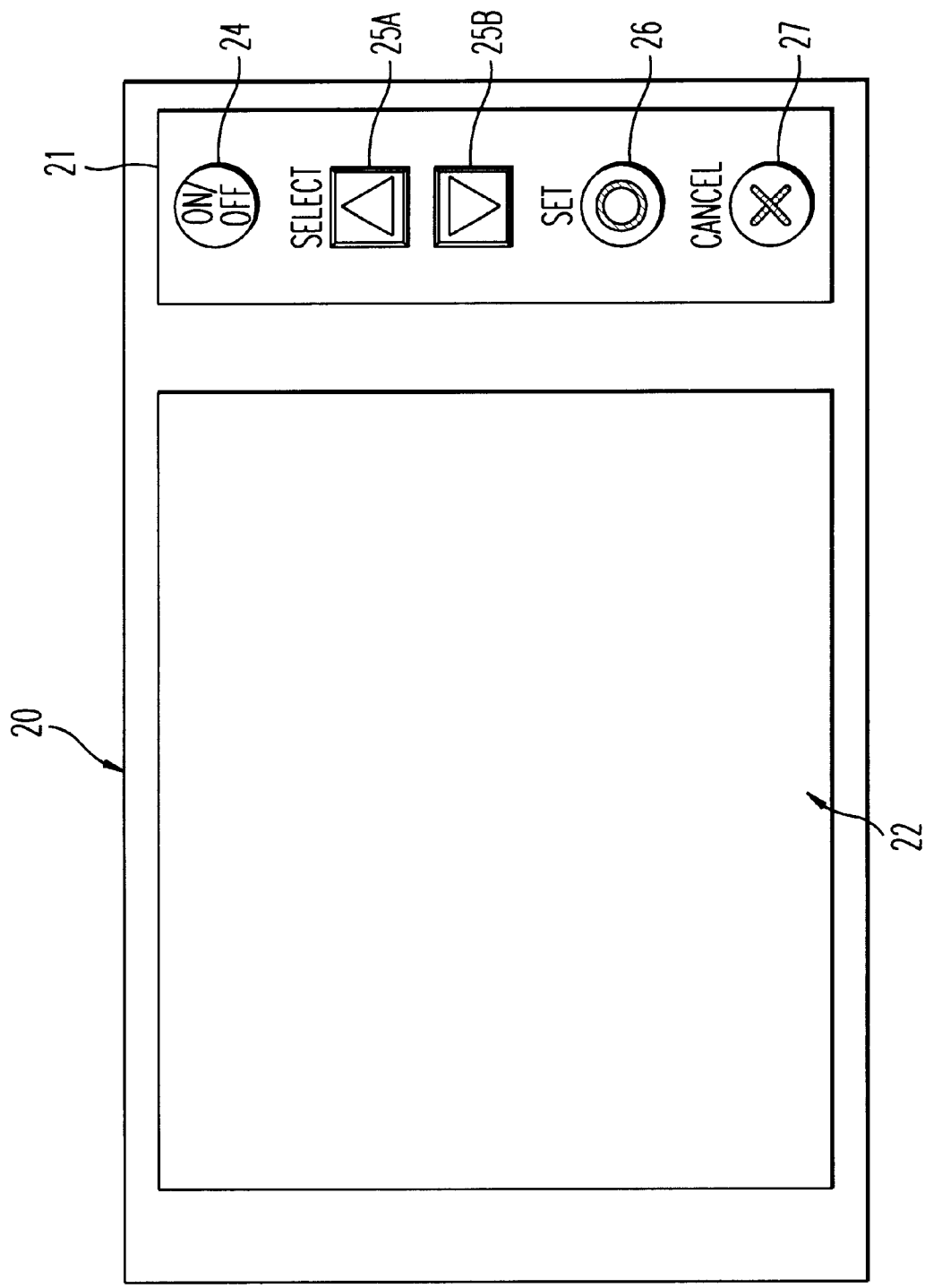
FIG. 2 is a plan view showing an operation panel of the massaging apparatus.
Figure 3:
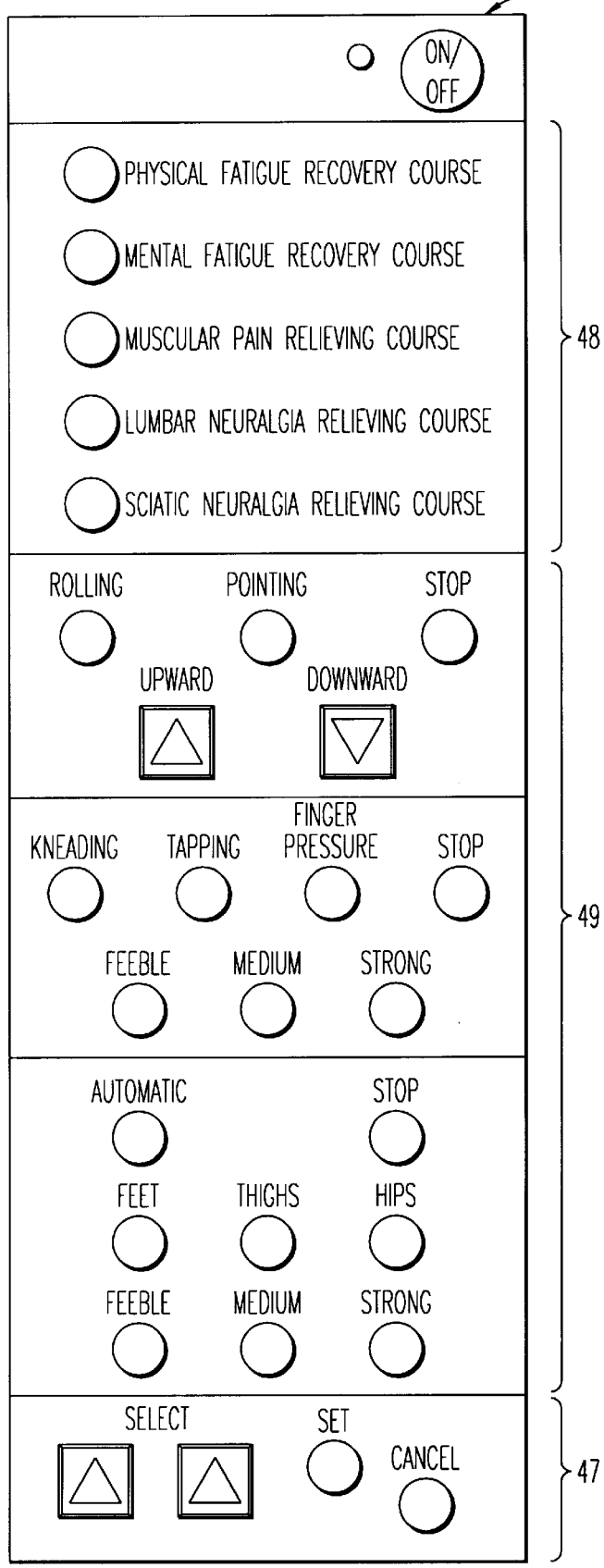
FIG. 3 is a plan view showing a remote control device of the massaging apparatus.

An operation panel 20 is attached to one of the right and left armrest portions 8 for the user to operate the massaging apparatus 1. As shown in FIG. 2, the operation panel 20 includes an operating part 21 having different switches, and a display part 22 for displaying various images. The operating part 21 includes power ON/OFF switch 24, selection switches 25A and 25B, setting switch 26, and canceling switch 27. The display part 22 comprises a liquid display device. The massaging apparatus 1 may otherwise be operated by a remote controller 28 as shown in FIG. 3.

Figure 4:
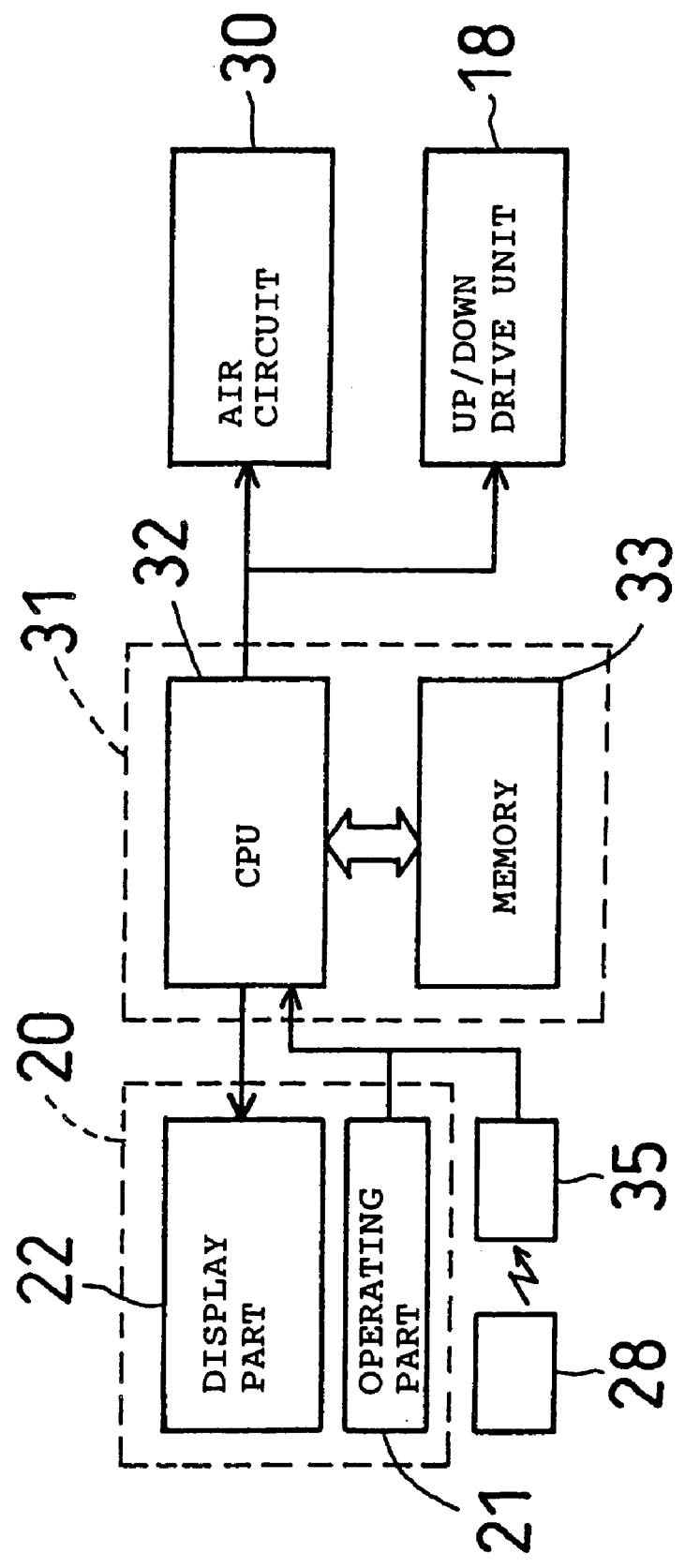
FIG. 4 is a block diagram showing a control system configuration of the massaging apparatus.

The massaging apparatus 1 thus constructed is controlled according to the control system shown in the block diagram of FIG. 4. Air circuit 30 for actuating each air cell 3 and the up/down drive unit 18 for raising and lowering the movable support 14 are controlled by control unit 31. The control unit 31 mainly comprises CPU 32 and memory 33. In response to an instruction from the operation panel 20 or that received by a signal reception part 35 from the remote controller 28, the CPU 32 executes a corresponding program stored in the memory 33 to control the air circuit 30 and the like. Specifically, the air supply/discharge change-over valves in the air circuit 30 are controlled. In this way, the control unit 31 serves also as execution means for executing massaging operations. As well, the control unit 31 controls image displaying operations of the display part 22.

Figure 5:
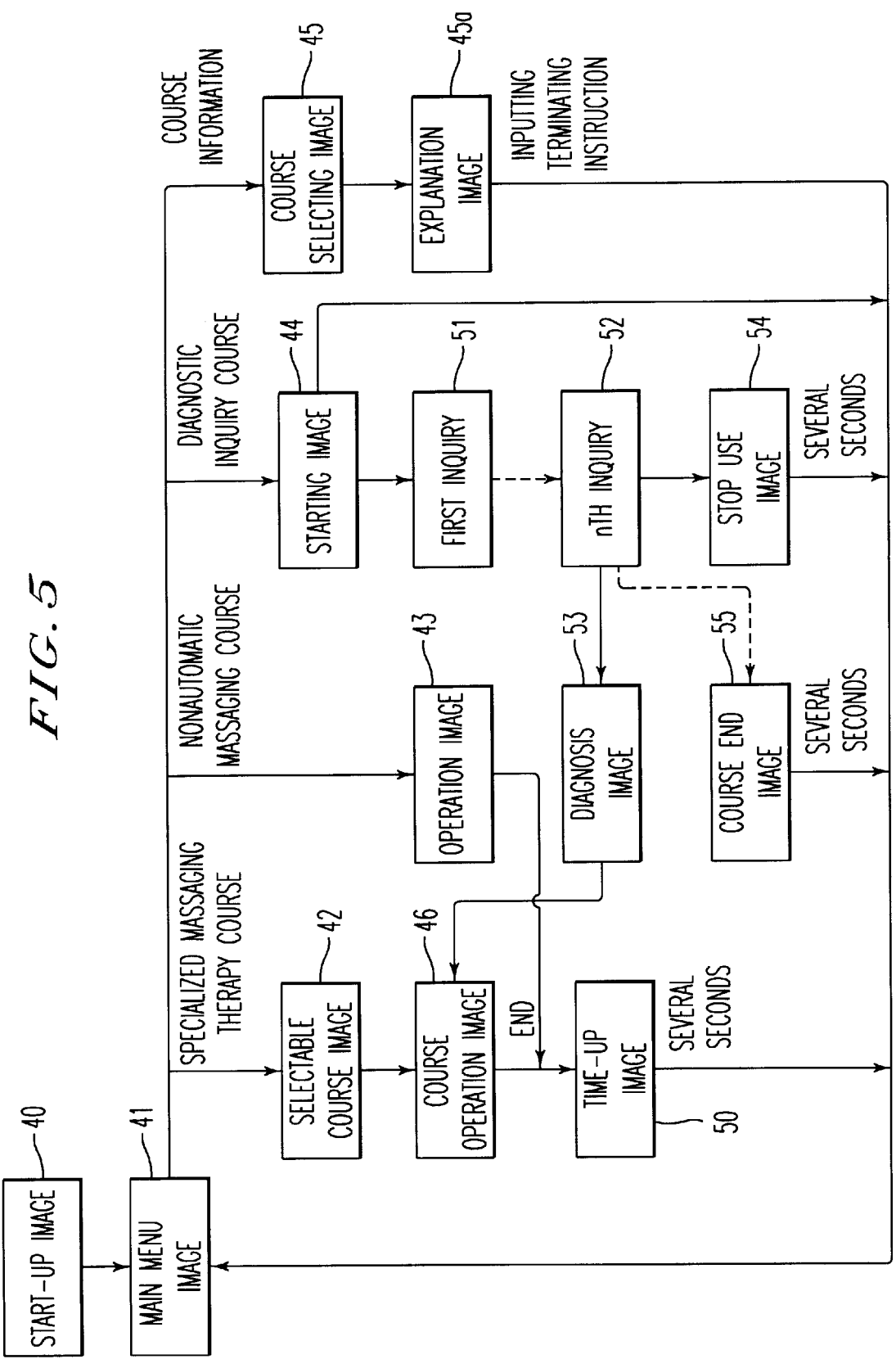
FIG. 5 is a flow-chart of the operation of the massaging apparatus represented as transition of display on the display part.

FIG. 5 is a flowchart of the operation of the massaging apparatus 1 represented as transition of display on the display part 22.

First, when the power ON/OFF switch 24 of the operating part 21 is turned ON, start-up image 40 is displayed on the display part 22 until the movable support 14 slides to its home position (for about 3 seconds).

Figure 6A:
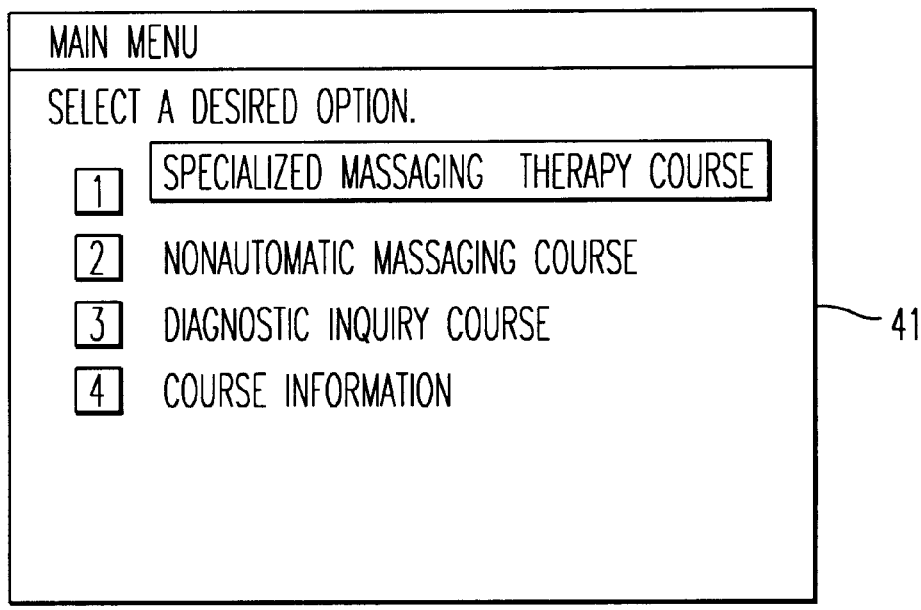
FIG. 6(a) shows an image presenting the main menu.

Subsequently, the display part 22 displays main menu image 41 presenting four options as shown in FIG. 6(a). Selection of a desired option is made through the switches 25, 26 and 27. The option thus selected is highlighted as shown.

Figure 6B:
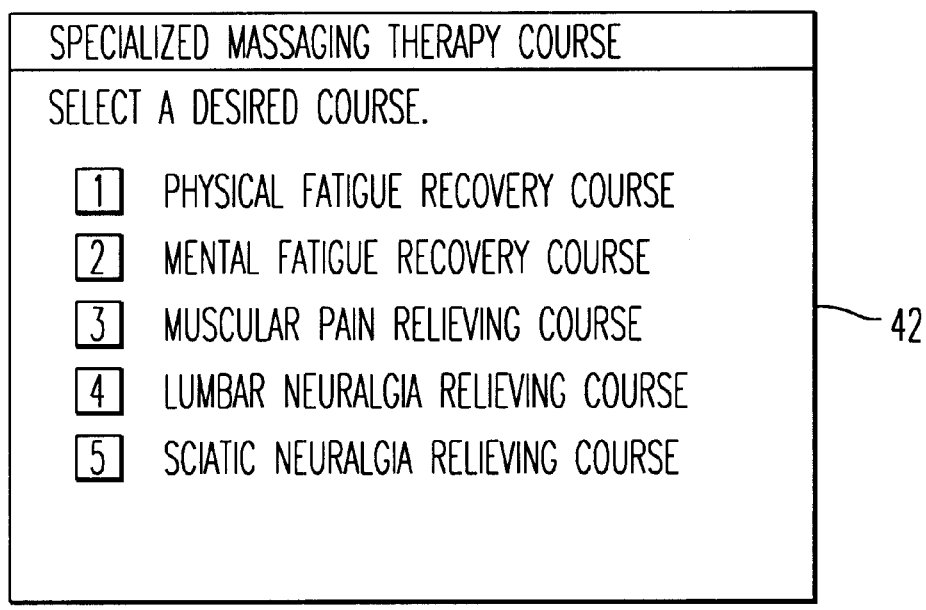
FIG. 6(b) shows an image presenting selectable specialized massaging therapy courses.

When the first option "SPECIALIZED MASSAGING THERAPY COURSE" is selected, selectable course image 42 presenting selectable specialized massaging courses as shown in FIG. 6(b) is displayed. The specialized massaging therapy courses are each a massaging course having a specific therapeutic purpose as indicated by its name. Program data of each specialized massaging therapy course by which a series of massaging operations for serving the respective purpose of the course is performed, is stored in the memory 33. When a desired one of the specialized massaging therapy courses is selected, the control unit 31 executes the program of the selected massaging therapy course to provide massaging operations according to the course. Thus, the control unit 31 serves also as execution means for executing a massaging course. During the execution of any one of the specialized massaging therapy courses, course operation image 46 presenting information on the massaging course in operation, including massaging conditions and a remaining operating time, is displayed on the display part 22 as shown in FIG. 7(c).

When the second option "NONAUTOMATIC MASSAGING COURSE" of the main menu 41 is selected, operation image 43 presenting information on the NONAUTOMATIC MASSAGING COURSE is displayed as shown in FIG. 6(c). The "NONAUTOMATIC MASSAGING COURSE" is a course in which the user can enjoy a desired massaging operation by manually inputting corresponding massaging conditions. The operation image 43 presents the massaging conditions of a massaging operation, which can be varied through the switches of the operating part 21 to perform another massaging operation.

When the SPECIALIZED MASSAGING THERAPY COURSE or the NONAUTOMATIC MASSAGING COURSE is completed, time-up image 50 indicating the completion of the course is displayed and several seconds thereafter the main menu image 41 resumes.

The remote controller 28 has switches 47 corresponding to the switches of the operating part 21, and in addition thereto, specialized massaging therapy course selecting switches 48 for selecting any one of the specialized massaging therapy courses without using the selectable course image 42 and nonautomatic massaging course switches 49 for setting conditions of a desired massaging operation without using the operation image 43.

Figure 7A:
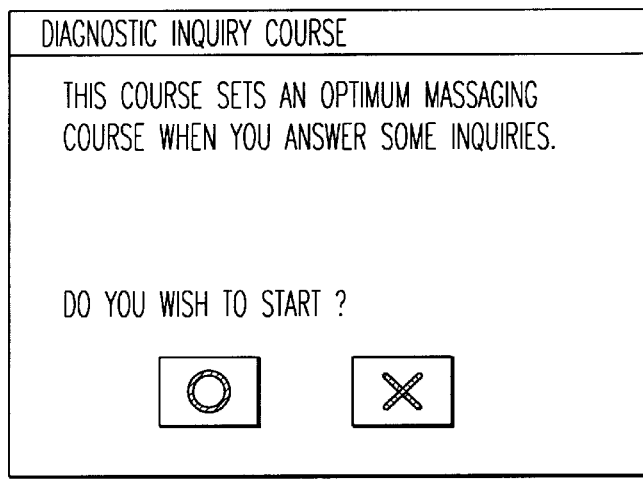
FIG. 7(a) shows a starting image of a diagnostic inquiry course.
Figure 7B:
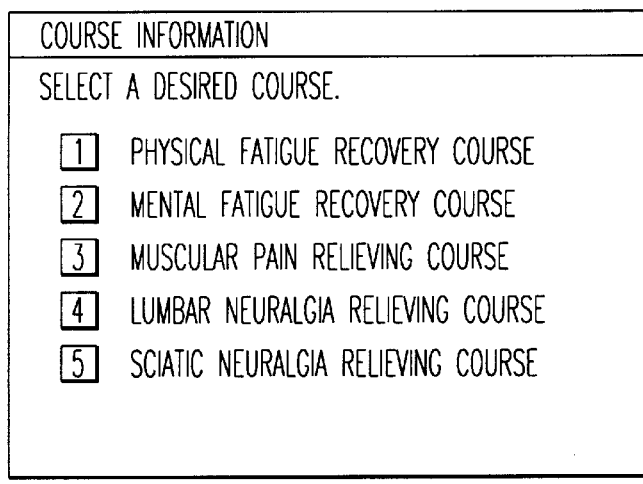
FIG. 7(b) shows an image presenting selectable massaging courses to be explained.
Figure 7C:
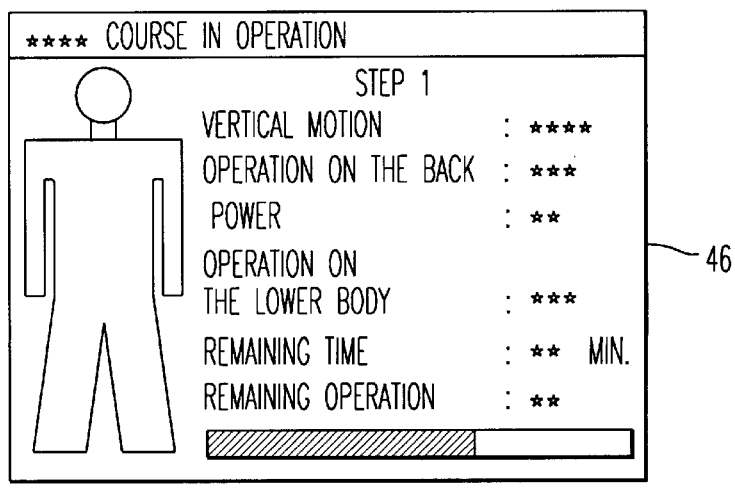
FIG. 7(c) shows an image presenting information on a massaging course in operation.

When the third option "DIAGNOSTIC INQUIRY COURSE" of the main menu 41 is selected, starting image 44 of the DIAGNOSTIC INQUIRY COURSE shown in FIG. 7(a) is displayed. In the DIAGNOSTIC INQUIRY COURSE the massaging apparatus 1 addresses a series of diagnostic inquiries to the user, judges the physical condition of the user based on user's answers, and sets a massage course meeting the user's physical condition thus judged. The DIAGNOSTIC INQUIRY COURSE will be described in detail later.

When the fourth option "COURSE INFORMATION" of the main menu 41 is selected, course selecting image 45 presenting the names of massaging courses to be selected for explanation displayed. The course information is information on the specialized massaging therapy courses. When any one of the massaging courses presented by the image 45 is selected, explanation image 45a explaining the massaging course selected is displayed.

The diagnostic inquiries are each a inquiry of the type which can be answered by choosing "YES" (corresponding to the setting switch 26) or "NO" (corresponding to the canceling switch 27) as shown in FIG. 8(a) and 8(b). Examples of specific diagnostic inquiries include, in addition to those appearing in the drawings, inquiries as to (1) whether the user is male or female, (2) whether or not the user has a catamenial pain, (3) whether or not the user has a headache, (4) whether or not the user has an eyestrain, (5) whether or not the user feels stiff in the back, (6) whether or not the user has a lumbago, (7) whether or not the user feels aching in the hips, (8) whether or not the user feels stiff in a calf, (9) whether or not the user is oversensitive to cold, (10) whether or not the user feels stiff in a shank, (11) whether or not the user has a swollen face in the early morning, (12) whether or not the user frequently feels thirsty, (13) whether or not the user frequently catches cold, (14) whether or not the user has a pain or feels heavy in and around the stomach, (15) whether or not the user has a pain in his or her side, (16) whether or not the user has a pain or feels heavy in the abdomen, (17) whether or not the user is constipated, and (18) whether or not the user has a diarrhea. These inquiries are only illustrative but not limitative. The diagnostic inquiries may include those concerning (a) general information such as age, height and weight, (b) the current physical condition, (c) the recent physical condition, (d) items for investigating a user's unrecognized latent tendency which are not related to the physical condition, and (e) the case history.

Such inquiries are displayed by the display part 22, which in turn is controlled by the control unit 31. Thus, the display part 22 and the control unit 31 function as diagnostic inquiry means.

The user answers each inquiry using the setting switch 26 or the canceling switch 27 of the operating part 21. Thus, the operating part 21 functions as input means for inputting a user's answer to a diagnostic inquiry.

The control unit 31 sets a specialized massaging therapy course suited to the user on the basis of the information obtained from a user's answer to a diagnostic inquiry. In setting the specialized massaging therapy course the control unit 31 judges the physical condition of the user based on the information obtained from the user's answer, and then selects the specialized massaging therapy course best-suited for amelioration of the physical condition of the user from a plurality of specialized massaging therapy courses and sets the selected course for execution.

As a simple example, where the user chooses "YES" in answer to a diagnostic inquiry asking whether or not the user has lumbago, the control unit 31 judges the user to have lumbago and selects "LUMBAR NEURALGIA RELIEVING COURSE" which is suited for lumbago. It should be noted that such judgment is not always made in such a simple way but may be a synthetic judgment made from answers to a plurality of diagnostic inquiries.

In this way the control unit 31 serves not only as judgment means for judging the physical condition of the user based on a user's answer but also as setting means for setting massaging conditions of a massage operation to be executed on the basis of the judgment of the user's physical condition. In this embodiment, although the judgment means and the setting means are composed of a computer program for implementing the foregoing functions and the control unit 31 adapted to execute the computer program, each of these means may be individually composed of an electronic circuit capable of achieving functions which are equivalent to those described above.

Figure 9A:
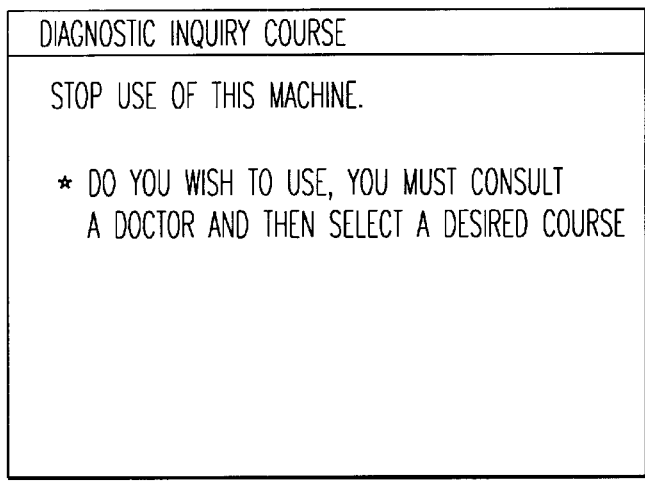
FIG. 9(a) shows an image advising stoppage of use of the massaging apparatus.

The control unit 31, as the judgment means, also judges whether or not the user is in a physical condition contraindicating any massage. This judgment is made based on a diagnostic inquiry presented in diagnostic inquiry image 52 as shown in FIG. 8(b). If the user chooses "YES" in answer to the inquiry, the control unit 31 judges the user to be in the massage contraindicating condition and, based on this judgment, causes the display part 22 to display stop use image 54 which urges the user to stop using the massaging apparatus 1 as shown in FIG. 9(a), without setting any massaging course. The display part 22 displays the stop use image 54 for several seconds and then resumes the main menu 41.

Preferably, the diagnostic inquiry shown in FIG. 8(b) for the judgment of the contraindicating condition is addressed prior to other diagnostic inquiries. In this case, if the user is judged to be in the massage contraindicating condition, there is no need to address any other inquiry and, hence, the DIAGNOSTIC INQUIRY COURSE can be terminated efficiently by displaying the stop use image 54 immediately after the judgment.

When a series of diagnostic inquiries (the first to nth inquiries) are completed, the control unit 31 judges the physical condition of the user and sets a suitable specialized massaging therapy course as described above, and then outputs diagnosis image 53 on the display part 22 to present a diagnostic judgment of the current physical condition of the user as output means for outputting information on the physical condition of the user. This physical condition information outputting function allows the user to know his or her own current physical condition.

Figure 9B:
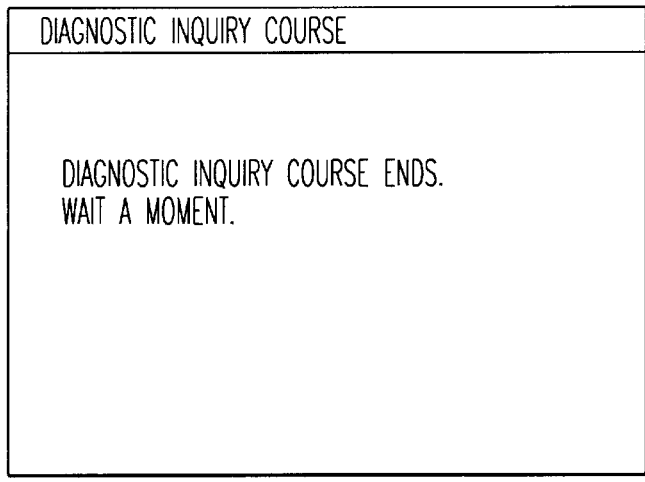
FIG. 9(b) shows an image indicating termination of the diagnostic inquiry course.

The diagnosis image 53 further presents a inquiry asking if the user wishes execution of the massaging therapy course thus set. If the user chooses "YES" in answer to this inquiry, the control unit 31 also serving as execution means executes the massaging therapy course thus set. In this case, the course operation image 46 presenting information on the operating conditions of the massaging therapy course in operation is displayed as in the SPECIALIZED MASSAGING THERAPY COURSE.

Where the user chooses "NO" in answer to the inquiry, course end image 55 as shown in FIG. 9(b) is displayed for several seconds, and then the main menu 41 is resumed. In this way it is possible for the user to utilize only the diagnostic function without executing any massage course. It is also possible to terminate the DIAGNOSTIC INQUIRY COURSE in the middle of the series of diagnostic inquiries by inputting a terminating instruction through the operating part 21 to display the course end image 55.

Figure 9C:
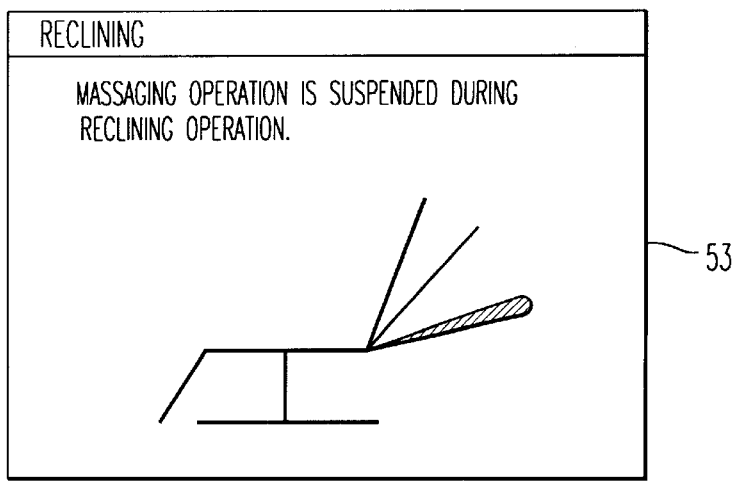
FIG. 9(c) shows an image of a reclining operation of the massaging apparatus.

The backrest portion 7 of the massaging apparatus 1 is reclinable as described above. During the reclining operation of the backrest portion 7 the control unit 31 suspends the massaging operation performed by the air cells 3 (massaging means). Specifically, when the reclining operation is started by operating a reclining switch (not shown), the control unit 31 (CPU 32) controlling the operation of the air cells 3 is interrupted to suspend the massaging operation, while the display part 22 displays reclining image 56 shown in FIG. 9(c) to inform the user that the massaging operation is suspended. When the reclining operation is completed, the display part 22 displays again the image that has been displayed prior to the reclining image 56 and the massaging operation is resumed. Since the load and position of the user on the backrest portion 7 are instable during the reclining operation, any massaging operation is not performed during the reclining operation in which the user is in an instable condition. In other words, the user can enjoy a stable massage.

While only a preferred embodiment of the present invention has been described in detail, as will be apparent for those skilled in the art, various modifications and variations can be made in embodiment without departing from the scope of the present invention.

For instance, the diagnosis image 53 may present, in addition to the diagnostic judgment of the current physical condition of the user, general advice including living guidance based on the current physical condition and general information on how to utilize the massaging apparatus based on the current physical condition.

The control unit 31 may be so constructed as to cause the display part 22 to display the diagnosis image 53 recommending a specialized massaging therapy course that meets the current physical condition of the user but not to set the specialized massaging therapy course based on the judgment of the current physical condition of the user, and then allow the user to manually input an instruction to execute the recommended specialized massaging therapy course. Alternatively, it is possible to provide an arrangement such that the diagnosis image 53 does not recommend any specialized massaging course but indicates the portions to be massaged and the manner of massage (kneading, tapping or the like) to be performed, and then the user is allowed to manually input appropriate massaging conditions through the operation image 43 of the NONAUTOMATIC MASSAGING COURSE.

Where the control unit 31 is adapted to set any one of the specialized massaging therapy courses, the selected specialized massaging therapy course may be partially changed depending on the physical condition of the user and set. For instance, assuming that a certain specialized massaging therapy course includes a step of kneading the shoulders of a user at a strength of X for Y seconds and that the user is judged to be in a physical condition requiring an intensive massage on the shoulders, the initial values X and Y may be varied to, for example, X+1 and Y+10, respectively, to massage the shoulders of the user more intensively.

Alternatively, the control unit 31 as the setting means may be adapted to compose a therapy course by combining appropriate massaging conditions based on the judgment of the physical condition of the user and set it instead of selecting and setting one of the predetermined therapy courses presented by the selectable course image 42.

The diagnostic inquiry means and the input means may be such that the addressing of diagnostic inquiries and the inputting of answers are achieved on a dialogic basis through voice instead of the image display and the operation of switches. In this case various other operations may also be achieved on a dialogic basis through voice.

The massaging apparatus 1 may be provided with storage means for storing information (user's answer) obtained in the diagnostic inquiry step for such information to be utilized in the next massage.

The massaging operation may be performed on a motor-drive basis instead of using the air cells.

Further, the massaging apparatus may be of any other form such as a mattress form than the chair form.

What is claimed is:

1. A massaging apparatus comprising:
   a massaging element configured to perform a massaging action;
   a drive mechanism positioned and configured to move the massaging element;
   diagnostic inquiry means for addressing at least one diagnostic inquiry to a user;
   input means for inputting a user's answer to the at least one diagnostic inquiry;
   judgment means for judging the physical condition of the user based on the user's answer;
   setting means for setting a massage operation based on the judgment made by the judgment means; and
   execution means for causing the drive mechanism to drive the massaging element according to the massage operation set by the setting means.

2. A massaging apparatus as set forth in claim 1, wherein the judgment means is capable of judging the physical condition of the user to be contraindicating any massages.

3. A massaging apparatus as set forth in claim 2, wherein the setting means does not set any massage operations when the judgment means judges the physical condition of the user to be contraindicating any massages.

4. A massaging apparatus as set forth in claim 1, further comprising output means for outputting information on the physical condition of the user based on the judgment made by the judgment means so as to allow the user to know the information.

5. A massaging apparatus as set forth in claim 2, further comprising output means for outputting information on the physical condition of the user based on the judgment made by the judgment means so as to allow the user to know the information.

6. A massaging apparatus as set forth in claim 3, further comprising output means for outputting information on the physical condition of the user based on the judgment made by the judgment means so as to allow the user to know the information.

7. A massaging apparatus capable of performing a plurality of predetermined massaging courses each including a series of massage operations, comprising:
   a massaging element configured to perform the series of massage operations;
   a drive mechanism positioned and configured to move the massaging element;
   diagnostic inquiry means for addressing a diagnostic inquiry to a user, the diagnostic inquiry including an inquiry required for selection of one of the plurality of predetermined massaging courses which meets the physical condition of a user;
   input means for inputting a user's answer to the diagnostic inquiry;
   setting means for selecting and setting said one of the plurality of predetermined massaging courses based on the user's answer; and
   execution means for causing the drive mechanism to move the massaging element in conformity with said one of the plurality of predetermined massaging courses.

8. A massaging apparatus comprising:
- a plurality of massaging elements each configured to perform a massaging action;
- a drive mechanism positioned and configured to move at least one of the plurality of massaging elements;
- diagnostic inquiry means for addressing at least one diagnostic inquiry to a user;
- input means for inputting a user's answer to the at least one diagnostic inquiry;
- judgment means for evaluating the user's answer and judging the physical condition of the user;
- setting for setting a massage operation including at least one massage action based on a judgment made by said judgment means; and
- execution means for causing said drive mechanism to move said at least one of said plurality of massaging elements according to the massage operation set by said setting means.

9. A massaging apparatus as set forth in claim 8, wherein said diagnostic inquiry means includes a visual display positioned and configured to display said at least one inquiry.

10. A massaging apparatus as set forth in claim 8, wherein said diagnostic inquiry means includes an audio device positioned and configured to address the at least one inquiry audibly.

11. A massaging apparatus as set forth in claim 8, wherein said massaging element comprises at least one air cell.

12. A massaging apparatus as set forth in claim 8, wherein said massaging element comprises at least one motor drive.

13. A massaging apparatus as set forth in claim 8, further comprising output means for outputting information on the physical condition of the user based on the judgment made by the judgment means, wherein the output means provides the user with the information.

14. A massaging apparatus as set forth in claim 8, wherein said setting means sets up for a massage operation desired by the user.

15. A massaging apparatus as set forth in claim 8, wherein said at least one inquiry comprises a question whose answer is either "yes" or "no".

16. A massaging apparatus as set forth in claim 8, wherein said at least one inquiry comprises a series of inquiries whose answers are either "yes" or "no".

17. A massaging apparatus as set forth in claim 16, wherein said diagnostic inquiry means and judgement means interact such that once said judgement means reaches a judgement unfavorable to any massages, said diagnostic inquiry means terminates remaining ones of the series of inquiries and sends a massage informing the user of the judgement.

18. A massaging apparatus as set forth in claim 8, further comprising storage means for storing the user's answer, wherein said judgement means utilizes the user's answer in a next massage operation.

19. A massaging apparatus as set forth in claim 8, wherein said judgment means is capable of judging the physical condition of the user to be contraindicating any massages.

20. A massaging apparatus as set forth in claim 19, wherein said setting means does not set any massaging actions when said judgement means judges the physical condition of the user to be contraindicating any massages.

* * * * *